(12) United States Patent
Panelli

(10) Patent No.: US 7,676,378 B2
(45) Date of Patent: Mar. 9, 2010

(54) METHOD AND APPARATUS FOR PERFORMING ECONOMIC ANALYSIS OF A RADIOLOGICAL IMAGE ARCHIVING SYSTEM

(75) Inventor: Edward J. Panelli, Chicago, IL (US)

(73) Assignee: General Electric Company, Niskayuna, NY (US)

( * ) Notice: Subject to any disclaimer, the term of this patent is extended or adjusted under 35 U.S.C. 154(b) by 2697 days.

(21) Appl. No.: 09/683,791

(22) Filed: Feb. 14, 2002

(65) Prior Publication Data

US 2003/0154102 A1    Aug. 14, 2003

(51) Int. Cl.
G06Q 10/00       (2006.01)
G06Q 50/00       (2006.01)

(52) U.S. Cl. .................. 705/2; 705/3; 705/4; 707/104; 707/204; 713/400

(58) Field of Classification Search ................. 382/128; 707/3–5, 104, 204; 600/300; 705/2–4, 26; 713/400

See application file for complete search history.

(56) References Cited

U.S. PATENT DOCUMENTS

| | | | | |
|---|---|---|---|---|
| 5,185,696 A | * | 2/1993 | Yoshino et al. | 705/36 R |
| 5,321,520 A | * | 6/1994 | Inga et al. | 358/403 |
| 5,655,084 A | * | 8/1997 | Pinsky et al. | 705/3 |
| 6,006,191 A | * | 12/1999 | DiRienzo | 705/2 |
| 6,226,625 B1 | * | 5/2001 | Levenstein | 705/400 |
| 6,260,021 B1 | * | 7/2001 | Wong et al. | 705/2 |
| 6,349,373 B2 | * | 2/2002 | Sitka et al. | 711/161 |
| 6,574,742 B1 | * | 6/2003 | Jamroga et al. | 713/400 |
| 6,820,100 B2 | * | 11/2004 | Funahashi | 707/204 |
| 7,007,274 B1 | * | 2/2006 | Patel et al. | 717/176 |
| 2002/0042751 A1 | * | 4/2002 | Sarno | 705/26 |
| 2002/0082963 A1 | * | 6/2002 | Corvin | 705/36 |

OTHER PUBLICATIONS

Dan Balaban, Pineers Assess The Role Java Can Play in Health Care, Health Data Management, New York, Jul. 1998, vol. 6, issue 7, p. 63-68.*

* cited by examiner

*Primary Examiner*—Gerald J. O'Connor
*Assistant Examiner*—Linh-Giang Michelle Le
(74) *Attorney, Agent, or Firm*—Fletcher Yoder

(57) ABSTRACT

An electronic system is featured to enable a radiological image archiving system supplier to provide a customer with economic data regarding a supplier's radiological image archiving system. The system is operable to direct a query page to the customer via an electronic communication system. The query page provides the customer with at least one question. The at least one question is designed so that the answer(s) to the at least one question enables the system to establish expected cost reductions resulting from the use of the supplier's radiological image archiving system over the use of the customer's existing archival system. The answer(s) also may be used to enable the system to establish a recommended radiological image archiving system for the customer. The answer(s) also may be used to establish a payback period for the recommended radiological image archiving system based on the expected cost reductions resulting from the use of the supplier's radiological image archiving system and the cost of the recommended system.

10 Claims, 3 Drawing Sheets

FIG. 3

**RADIOLOGICAL IMAGE ARCHIVING SYSTEM
JUSTIFICATION CONFIGURATOR**

PLEASE FILL OUT THE FOLLOWING INFORMATION:

HOW MANY EXAMS / DAY  [         ] EXAMS
HOW MANY IMAGES / EXAM [         ] IMAGES
HOW MANY MB / IMAGE [         ] MBs
HOW MANY WORKDAYS / YEAR [         ] DAYS

[EXECUTE CALCULATION]  [RESET VALUES]

FIG. 4

**RADIOLOGICAL IMAGE ARCHIVING SYSTEM
JUSTIFICATION CONFIGURATOR**

PLEASE FILL OUT THE FOLLOWING INFORMATION:

HOW MANY EXAMS / DAY  [ 20 ] EXAMS
HOW MANY IMAGES / EXAM [ 300 ] IMAGES
HOW MANY MB / IMAGE [ .5 ] MBs
HOW MANY WORKDAYS / YEAR [ 300 ] DAYS

[EXECUTE CALCULATION]  [RESET VALUES]

RADIOLOGICAL IMAGE ARCHIVING SYSTEM JUSTIFICATION CONFIGURATOR

PLEASE FILL OUT THE FOLLOWING INFORMATION:

| | | |
|---|---|---|
| HOW MANY EXAMS / DAY | 20 | EXAMS |
| HOW MANY IMAGES / EXAM | 300 | IMAGES |
| HOW MANY MB / IMAGE | .5 | MBs |
| HOW MANY WORKDAYS / YEAR | 300 | DAYS |

[ EXECUTE CALCULATION ]   [ RESET VALUES ]

STORAGE:

| | | |
|---|---|---|
| TOTAL GB / YEAR | 900 | GB |
| ONLINE STORAGE | 1.8 | MONTHS |
| 120 CD | 2 | MONTHS |
| 480 CD | 8.2 | MONTHS |
| 1 TB DLT | 26 | MONTHS |

ESTIMATED MOD (1.3 GB) COSTS:

| | |
|---|---|
| 692 | DISKS PER YEAR |
| $69,230.00 | COST OF DISKS / YEAR |
| 15 | FILM PER EXAM (20 UP) |
| $1.00 | $ SHEET OF FILM |
| $99,000.00 | COST OF FILM / YEAR |
| $168,230.00 | COST OF FILM AND MOD / YEAR |

SAVINGS:

| | |
|---|---|
| 3 | FILM PER EXAM |
| $1.00 | $ SHEET OF FILM |
| $19,800.00 | COST OF FILM / YEAR |
| $79,200.00 | FILM SAVINGS / YEAR |
| $69,230.00 | MOD SAVINGS / YEAR |
| $148,430.00 | TOTAL SAVINGS / YEAR |

SUGGESTED CONFIGURATION:

| | |
|---|---|
| $195,000.00 | SUGGESTED RADIOLOGICAL IMAGE ARCHIVE SYSTEM |
| 15 | MONTHS TO PAYBACK |
| $6,388.00 | MONTHLY LEASE PAYMENTS (36 MONTH LEASE) |

FIG. 5

METHOD AND APPARATUS FOR PERFORMING ECONOMIC ANALYSIS OF A RADIOLOGICAL IMAGE ARCHIVING SYSTEM

BACKGROUND OF INVENTION

The present invention relates generally to a method and apparatus for providing purchasing information to a customer for storage of radiological images, and more particularly, to a method and apparatus to enable a customer that stores radiological images on film to perform an economic analysis of converting to a digital radiological image storing system.

Traditionally, medical diagnostic images are recorded by exposing an imaging plate to a source of penetrating radiation. To view the image on the imaging plate, the imaging plate or a recording of the image on the imaging plate, are physically brought to the viewer. Typically, numerous film copies of the imaging plate are produced. Typically, multiple copies are produced so that they may be viewed by a number of different medical personnel, such as radiologists, the patient's primary care physician, specialists, and so forth. Archival film copies of the imaging plates are also produced. The archival copies may be stored as part of a patient's medical record, or otherwise, for years. Filmed images may be converted to a digital format by a scanner, or reader. Additionally, many radiological devices are now operable to produce digital images for viewing on a radiological viewing station. These digital images may be stored on an optical disc system for long-term storage, such as archiving.

A digital radiological image storage system has been developed to archive images electronically. The radiological images may be viewed on a radiological imaging workstation coupled to an electronic radiological viewing system. The digital radiological image storage system reduces the number of film copies of a radiological image that must be produced.

For commercialization and marketing purposed, a customer may contact a supplier of digital radiological image storage systems to request information regarding the supplier's radiological image storage system. Alternatively, a radiological image storage system supplier may contact a customer in hopes of generating sales of radiological image storage systems. However, there are problems associated with exchanging information in these verbal transactions. For example, both parties in each of these cases may consume significant amounts of time attempting to elicit basic information from the other. For example, it may take a radiological image storage system supplier a significant amount of time simply to establish the customer's basic radiological imaging workstation needs or desires. Additionally, a customer may expend significant amounts of time obtaining basic information about the digital radiological image storage systems available from the supplier. Indeed, the customer may consume time receiving information from a supplier about digital radiological image storage systems that are simply not suited for the customer's needs or desires.

There is a need for an improved technique for providing a digital radiological image storage system customer with purchasing information regarding a supplier's digital radiological image storage systems prior to contact between a sales representative of the supplier and the customer. There is a particular need for a system or method that provides a customer with data regarding the costs and benefits of purchasing a digital radiological image storage system.

SUMMARY OF INVENTION

According to one aspect of the present invention, an electronic system is featured to enable a radiological image archiving system supplier to provide a customer with economic data regarding a supplier's radiological image archiving system in response to data provided by the customer. The system directs a query page to the customer via an electronic communication system. The query page provides the customer with a plurality of questions. The plurality of questions are designed so that the answers to the questions enable the system to establish a portion of a customer's current operational costs for an existing radiological image archiving system. Additionally, the answers may be used to enable the system to establish savings in the customer's current operational costs that may be produced with a radiological image archiving system provided by the supplier. In addition, the answers may be used to enable the system to establish a recommended radiological image archiving system for the customer. The answers may also be used to establish a payback period for the recommended radiological image archiving system based on the savings in the customer's operational costs and the cost of the recommended system.

BRIEF DESCRIPTION OF DRAWINGS

FIG. 3 is a representation of a blank query webpage from a digital radiological image archiving system supplier, in accordance with certain aspects of the present technique;

FIG. 4 is a representation of the query webpage of FIG. 3, having data provided by a customer for submission to the supplier's system, in accordance with certain aspects of the present technique; and FIG. 5 is a representation of a webpage from a digital radiological image archiving system supplier providing economic data based on the data provided by the customer, in accordance with certain aspects of the present technique.

DETAILED DESCRIPTION

Figures 1, 2:
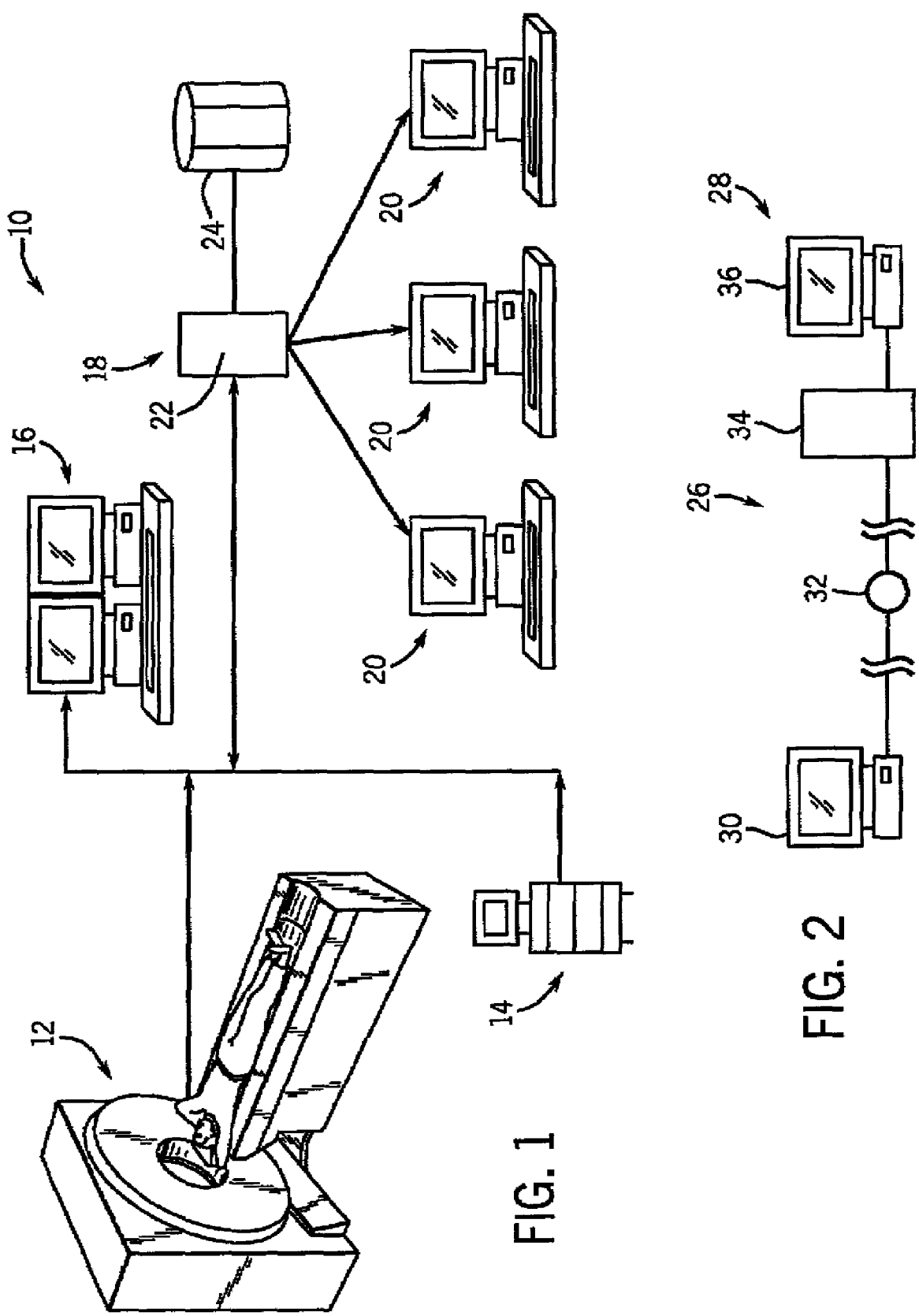
FIG. 1 is a diagrammatical representation of an electronic radiological imaging viewing and archiving system, in accordance with certain aspects of the present technique.
FIG. 2 is a diagrammatical representation of a system to enable a digital radiological image archiving system supplier to provide a digital radiological image storage system customer with economic date for a digital radiological image archiving system, in accordance with certain aspects of the present technique.

FIG. 1 illustrates a picture archive and communication system or PACS 10 for receiving, compressing and decompressing image data. In the illustrated embodiment, PACS 10 receives image data from several separate imaging systems designated by reference numerals 12 and 14. As will be appreciated by those skilled in the art, the imaging systems may be of various type and modality, such as magnetic resonance imaging (MR) systems, computed tomography (CT) systems, positron emission tomography (PET) systems, radio fluoroscopy (RF), ultrasound systems, and so forth. Moreover, the systems may include computed radiography (CR) systems or other digitizing stations designed to provide digitized image data from existing film or hard copy images. It should also be noted that the systems supplying the image data to the PACS may be located locally with respect to the PACS, such as in the same institution or facility, or may be entirely remote from the PACS, such as in an outlying clinic or affiliated institution. In the latter case, the image data may be transmitted via any suitable network link, including open networks, proprietary networks, virtual private networks, and so forth.

PACS 10 may comprise a diagnostic workstation 16 to enable a user to access and manipulate images from one or more of the imaging systems. Additionally, PACS 10 comprises a digital archiving system 18 designed to receive and process image data, and to make the image data available for review. The digital archiving system 18 also is coupled to reviewing workstations 20 at which a radiologist, physician, or clinician may access and view image data from the server 18. The reviewing workstations 20 will typically include a computer monitor, a keyboard, as well as other input devices, such as a mouse. The reviewing workstation 20 enables the client to view and manipulate data from a plurality of imaging systems, such as MRI systems, CT systems, PET systems, RF, and ultrasound systems.

The digital archiving system 18 comprises a short-term storage system 22 and a long-term storage system 24. The archiving system 18 serves as the repository for large volumes of image data for backup and archiving purposes. The short-term storage system 22 comprises a server and a memory. Preferably, the server is a high-performance server and the memory is a RAID (Redundant Array of Independent Disks) storage system. The server system 22 also may associate image data, and other workflow information within the PACS by reference to one or more file servers. For example, the server system 18 may include a DICOM database server containing cross-referenced information regarding specific image sequences, referring or diagnosing physician information, patient information, background information, work list cross-references, and so forth. The information within the database server serves to facilitate storage and association of the image data files with one another, and to allow requesting clients to rapidly and accurately access image data files stored within the system.

The long-term storage system 24 is coupled to the short-term storage system 22 and may comprise a CD jukebox and/or a digital tape system. Other DICOM workstations, such as diagnostic workstation 16 and reviewing workstation 20 can retrieve images from the archive system. Techniques for transferring image data between the short-term storage system 22, and any memory associated with short-term storage system 22 forming a short term storage system, and long-term storage system 24, may follow any suitable data management scheme, such as to archive image data following review and dictation by a radiologist, or after a sufficient time has lapsed since the receipt or review of the image files.

Additionally, archiving system 18 may be coupled to one or more interfaces, such as a printer interface designed to access and decompress image data, and to output hard copy images via a printer or other peripheral. In the illustrated system, other components of the PACS system or institution may be integrated with the foregoing components to further enhance the system functionality.

Referring generally to FIG. 2, a system 26 to enable a digital radiological image archiving system supplier to provide a digital radiological image archiving system customer with economic date for a digital radiological image archiving system is illustrated. The system 26 enables a customer to access a supplier's electronic information system 28 via a computer 30, or other electronic device. The customer accesses the supplier's electronic information system 28 via an electronic communication network 32, such as the Internet. The supplier's electronic information system 28 may comprise a server 34 or other suitable electronic device to manage electronic communications and/or applications. In addition, the system 28 may comprise a workstation 36 to enable a user to operate the supplier's electronic information system 28. For example, the workstation 36 may be used to input data into the supplier's information system 28. The data may comprise updated economic data, such as a change in radiological imaging film or changes in the cost of radiological image archiving systems.

The applications for the supplier's electronic information system may be written in any suitable programming language. Preferably, the application is written in java script. 6. The programming code may be stored and run at a single station (e.g. at the supplier's electronic information system) or at multiple stations, such as a customer's computer.

Referring generally to FIG. 3, a representation of a webpage 38 transmitted from the supplier's electronic information system 28 to the customer's computer 30 via the electronic information system 32 is illustrated. The webpage 38 is adapted to elicit relevant information from the customer to enable the supplier's electronic information system 28 to ascertain an appropriate system for the customer. The illustrated webpage 38 has a number of queries 40 followed by fill-able boxes 42 to enable a customer to provide an answer to the query. For example, the illustrated webpage 38 has a query 44 to elicit how many exams per day the customer performs. The webpage also has a box 46 to enable the customer to input the number of exams. The illustrated webpage 38 also has a query 48 to elicit how many images the customer takes per examination, along with a box 50 to enable the customer to input the number of images. The illustrated webpage also has a query 52 to elicit how many MB (Megabytes) of memory are used to store each image, as well as box 54 to enable the customer to input the number of MB's. Finally, in the illustrated embodiment, the webpage 38 has a query 56 to elicit how many days per year that radiological images are obtained, as well as a box 58 to enable the customer to input the number of workdays per year. The queries 40 listed above are not an exclusive, or mandatory, list of queries that a supplier may provide on the webpage 38. A virtual button 60 is provided to direct the customer's computer 30 to send the data from the boxes 42 to the supplier's electronic information system 28 via the communication system 32 and process the data. A second virtual button 62 is provided to enable the customer to reset the data in the boxes 42.

Referring generally to FIG. 4, an example of a webpage 38 completed by a customer is illustrated. In the example webpage provided, the customer has indicated in box 46 that they perform 20 examinations per day. Additionally, in box 50 the customer has indicated that they take 300 images per exam. The customer has also indicated in box 54 that they use 0.5 MB's per image. Finally, the customer has indicated in box 58 that they take images 300 days per year.

Referring generally to FIG. 5, the customer has activated the virtual button 60 to send the data from the boxes 42 to the supplier's electronic information system 28. In addition, the supplier's electronic information system 28 has processed the data and transmitted the results to the customer's computer 30. In the illustrated embodiment, the supplier's electronic information system 28 has established the size in GB's (Gigabytes) needed for one year of images produced by the customer and provided this information in a box 64 on the webpage 38. In the example, the supplier's electronic information system 28 multiplied the data provided in boxes 46, 50, 54, and 58 to obtain the storage capacity needed for one year.

The supplier's electronic information system 28 also established the lengths of time of producing radiological images at the customer's rate of usage that various storage media could store radiological images. In the illustrated embodiment, the supplier's electronic information system 28 has established that the archiving system can store the images produced over a period of time in the server and provided this information in a box 66. In this example, based on the storage capacity of 900 GB's per year and the storage capacity of the online storage, the supplier's electronic information system 28 has established that the archiving system can store the images produces over a period of 1.8 months in the server. Additionally, in the illustrated embodiment, the supplier's electronic information system 28 has established that the archiving system can store the images produced over a period of time in a 120 CD jukebox and a 480 CD jukebox and provided the results in boxes 68 and 70, respectively. In this example, based on the storage capacity of 900 GB's per year and the storage capacity of the CD jukeboxes, the supplier's electronic information system 28 has established that the 120 CD jukebox can store the images produces over a period of approximately 2 months, and the 480 CD jukebox can store the images produces over a period of 8.2 months. Furthermore, in the illustrated embodiment, the supplier's electronic information system 28 has established that the archiving system can store the images produced over a period of time in a 1 TB digital tape system and provided the result in box 72. In this example, based on the storage capacity of 900 GB's per year and the storage capacity of the digital tape system, the supplier's electronic information system 28 has established that the digital tape system can store the images produces over a period of 26 months.

The supplier's electronic information system 28 also establishes costs that are associated with archiving radiological images using other archiving systems. For example, films degrade over time and require physical storage and transfer. Therefore, a storage system, such as an optical disc storage system, may be used to provide long-term archiving of the images. In the illustrated embodiment, the supplier's electronic information system 28 has established the cost of taking radiological images on film and archiving them on an optical disc storage system. In this embodiment, the supplier's electronic information system 28 has established the cost of film and optical discs for one year based on the usage data provided by the customer in boxes 46, 50, 54, and 58. The cost of optical discs is established by the storage capacity of one year of radiological imaging, provided in box 64, and the storage capacity of one optical disc, in this case 1.3 GB's. The number of optical discs needed for one year, 692, is provided in box 74 and the cost associated with the optical discs needed for one year, $69,230.00, is provided in box 76.

In this embodiment, the cost of film per year is established by multiplying the number of sheets of film needed per year by the cost of each sheet. The number of sheets of film needed per year is established from the number of sheets of film needed per exam and the number of exams performed per year. The number of sheets of film per exam is provided in box 78 and is established by dividing the number of images per exam, provided in box 50, by the number of images per sheet of film, e.g. 20. In this example, 15 sheets of film are needed per exam based on 300 images per exam and 20 images per sheet of film. The number of exams per year is established by multiplying the number of exams per day provided in box 46 by the number of workdays provided in box 58. The value associated with each sheet of film, estimated here at $1.00, used by the supplier's electronic information system 28 is provided in box 80. The cost of film per year is provided in box 82. In this example, the cost of film per year is $99,000.00. The sum of the annual optical disc costs, provided in box 76, and the annual film costs, provided in box 82, is provided in box 84.

In the illustrated embodiment, a certain number of copies of film are still produced. Therefore, there are some film costs associated with the digital radiological image archiving system. However, fewer film copies are made with a digital system because the images are readily accessible from the archiving system 18 on the viewing workstations 20. In this illustrated embodiment, rather than 15 sheets of film per exam, 3 sheets of film are needed per exam, as provided in box 86. For the same cost of each sheet of film, $1.00, and the same number of exams per year as the non-digital system, the digital radiological image archiving system has a cost of film per year of $19,800.00, as provided in box 90.

The savings in film costs per year using the digital radiological image archiving system, $79,200.00, is provided in box 92. This value is the difference in the film costs using a non-digital system, provided in box 90, and the film costs per year using the digital archiving system, provided in box 82. The cost of optical discs per year in a non-digital archiving system is provided again in box 94. The total savings resulting from the use of a digital radiological imaging system over that of a non-digital archiving system using optical discs is provided in box 96. This value, $148,430.00, is the sum of boxes 92 and 94.

The supplier's electronic information system 28 also provides a suggested digital radiological image archiving system based on the data received from the client and the cost of the system. The cost of the suggested system, $195,000.00, is provided in box 98. The supplier's electronic information system 28 also establishes a payback period for implementing the digital radiological system archiving system based on the cost of the suggested system and the savings in costs per year. The payback period in months is provided box 100. In this example, for the cost of $195,000.00 and the savings per year of $148,430.00, the payback period is approximately 15 months. In this embodiment, the supplier's electronic information system 28 also provides the cost of a monthly lease of the digital radiological image archiving system in box 102.

It can be seen that the system described above enables a radiological image archiving system manufacturer or supplier to electronically communicate with a customer to receive data from the customer and to provide the customer with economic data regarding a supplier's radiological image archiving system. For example, the system 26 enables a customer to use a computer 30 to communicate with a supplier's electronic information system 28 via an electronic communication network 32, such as the Internet. Additionally, the supplier's electronic information system 28 described above comprises a server 34, or other suitable electronic device, that enables the system 28 to communicate with the customer's computer 30 to provide webpages to the customer's computer 30 and receive the responses to the queries from the customer's computer 30. In addition, the server 34, or other suitable electronic device, is operable to process the data received from the customer and provide the customer's computer 30 with the resultant economic data.

It can also be seen that the applications stored in the supplier's electronic information system 28 may be used to enable the system to provide a variety of economic data to the customer, such as savings in the customer's current operational costs resulting from use of a radiological image archiving system provided by the manufacturer or supplier, as well as a recommended radiological image archiving system for the customer. Finally, an application stored in the supplier's electronic information system 28 to establish a payback period for the recommended radiological image archiving system based on the savings in the customer's operational costs and the cost of the recommended system may be seen from the system 28 described above.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An electronic information system, comprising:
   a query page stored in the electronic information system, wherein the electronic information system provides the query page to the customer via an electronic communication system, wherein the query page comprises at least one question designed, when completed by the customer, to enable the information system to establish an amount of radiological imaging film consumed by a customer over a specified period of time; and
   an application stored in the electronic information system, wherein the application establishes an expected reduction in radiological imaging film consumption due to use of a radiological image archiving system provided by a supplier of radiological image archiving systems.

2. The system as recited in claim 1, wherein the application establishes an expected cost reduction based on the expected reduction in archival radiological imaging film consumption.

3. The system as recited in claim 1, wherein the radiological imaging arching system provided by the supplier stores radiological images in a film-less format.

4. The system as recited in claim 2, wherein the application establishes an expected cost of the radiological image archiving system provided by the supplier.

5. The system as recited in claim 3, wherein the expected cost is based on the amount of radiological imaging system usage by the customer.

6. The system as recited in claim 4, wherein the application establishes a payback period for the radiological image archiving system based on the expected cost reduction and the expected cost of the radiological image archiving system.

7. An electronic information system, comprising:
   a query page stored in the electronic information system, wherein the electronic information system provides the query page to the customer via an electronic communication system, wherein the query page comprises at least one question designed, when completed by the customer, to enable the information system to establish an amount of storage capacity in a digital radiological image archiving system corresponding to an amount of radiological images produced by a customer over a specified time period.

8. The system as recited in claim 7, comprising an application stored in the electronic information system, wherein the application establishes an expected cost savings associated with storing radiological images in a digital radiological imaging system.

9. The system as recited in claim 8, wherein the application establishes an expected cost savings based on a decrease in radiological imaging film consumption using the digital radiological image archiving system.

10. The system as recited in claim 8, wherein the application establishes an expected cost savings based on a decrease in optical disc consumption for archiving of radiological images.

* * * * *